US008283491B2

(12) United States Patent
Campbell et al.

(10) Patent No.: US 8,283,491 B2
(45) Date of Patent: Oct. 9, 2012

(54) ISOMERIZED ALPHA OLEFIN SULFONATE AND METHOD OF MAKING THE SAME

(75) Inventors: Curtis Bay Campbell, Hercules, CA (US); Theresa Ann Denslow, Concord, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 508 days.

(21) Appl. No.: 12/256,672

(22) Filed: Oct. 23, 2008

(65) Prior Publication Data

US 2009/0112014 A1 Apr. 30, 2009

Related U.S. Application Data

(60) Provisional application No. 60/982,847, filed on Oct. 26, 2007.

(51) Int. Cl.
*C07C 309/20* (2006.01)
*C07C 303/06* (2006.01)

(52) U.S. Cl. ............ 562/30; 562/33; 562/108; 562/110; 562/112; 562/114; 562/123

(58) Field of Classification Search ........................ None
See application file for complete search history.

(56) References Cited

U.S. PATENT DOCUMENTS

| | | | | |
|---|---|---|---|---|
| 3,781,339 | A * | 12/1973 | Tuvell et al. | 562/30 |
| 4,059,620 | A * | 11/1977 | Johnson, Jr. | 562/123 |
| 4,562,727 | A * | 1/1986 | Dilgren et al. | 73/60.11 |
| 5,922,922 | A | 7/1999 | Harris et al. | |
| 6,337,310 | B1 * | 1/2002 | Campbell et al. | 508/391 |
| 6,506,717 | B1 | 1/2003 | Kott et al. | |
| 6,730,750 | B2 | 5/2004 | Eaton et al. | |
| 6,911,505 | B2 | 6/2005 | Small | |
| 7,655,827 | B2 * | 2/2010 | Ching et al. | 585/666 |
| 2007/0100192 | A1 * | 5/2007 | Harmer et al. | 585/665 |
| 2007/0118007 | A1 * | 5/2007 | Fong et al. | 585/511 |

OTHER PUBLICATIONS

B. Elvers; Ullmann's Encylopedia of Industrial Chemistry; 1989, pp. 243-247 and 275-276; vol. A13; Wiley-VCH Verlag GmbH & Co. KGaA.

Rosemarie Szostak; Handbook of Molecular Sieves; 1992; Van Nostrand Reinhold; New York.

Boy Cornils, Wolfgang A. Herrmann; Applied Homogeneous Catalysis with Organometallic Compounds; 1996; pp. 245-258; vol. 1; John Wiley & Sons, Incorporated, New Jersey.

* cited by examiner

*Primary Examiner* — Fiona T Powers
(74) *Attorney, Agent, or Firm* — Josetta I. Jones

(57) ABSTRACT

The present invention is directed to an isomerized alpha olefin sulfonate and a method of making the same wherein the isomerized alpha olefin sulfonate is derived from sulfonating an isomerized alpha olefin with sulfur trioxide in the presence of air thereby producing an isomerized alpha olefin sulfonic acid, wherein the isomerized alpha olefin is derived from the isomerization of $C_{12}$-$C_{40}$ normal alpha olefins; and neutralizing the isomerized alpha olefin sulfonic acid with a source of a mono-valent cation.

5 Claims, No Drawings

ISOMERIZED ALPHA OLEFIN SULFONATE AND METHOD OF MAKING THE SAME

This application claims priority from U.S. Provisional Application No. 60/982,847 filed on Oct. 26, 2007, the entire contents of which are incorporated herein by reference.

The present invention is directed to an isomerized alpha olefin sulfonate and a method of making the same.

BACKGROUND OF THE INVENTION

Alpha-olefins, especially those containing about 6 to about 20 carbon atoms, are important items of commerce, with about 1.5 million tons reportedly being produced in 1992. Alpha-olefins are also used as intermediates in the manufacture of detergents, as monomers (especially in linear low density polyethylene), and as intermediates for many other types of products. Alpha-olefins may also be employed in the oilfield drilling fluids market. The use of alpha-olefins as such, and alpha-olefins isomerized to internal olefins, has increased in recent years. As a consequence, improved methods of making these compounds are of value.

Most commercially produced alpha-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243-247 and 275-276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245-258. The major types of commercially used catalysts are alkylaluminum compounds, certain nickel-phosphine complexes, and a titanium halide with a Lewis acid such as diethylaluminum chloride (DEAC). In all of these processes significant amounts of vinylidene and/or tri-substituted and/or internal olefins and/or diolefins, can be produced depending on the carbon number of the olefin and the specific process. Since in most instances these are undesired, and often difficult to separate from the desired linear alpha-olefins, minimization of these byproducts is sought. Small, U.S. Pat. No. 6,911,505 discloses processes for the production of alpha-olefins, including dimerization and isomerization of olefins using a cobalt catalyst complex are provided herein. The olefins so produced are described in this patent as being useful as monomers in further polymerization reactions and useful as chemical intermediates.

Eaton, et al., U.S. Pat. No. 6,730,750, is directed to improved drag reducing agents and methods of forming improved drag reducing agents comprising the steps of isomerizing olefin monomers to form isomerized olefin monomers, polymerizing the isomerized olefin monomers in the presence of at least one catalyst to form a polyolefin drag reducing agent having unexpectedly superior drag reduction properties when combined with liquid hydrocarbons, such as viscous crude oil. This patent further discloses that the drag reducing agents may be introduced into conduits, such as pipelines, to increase the flow of the hydrocarbons through the conduit.

SUMMARY OF THE INVENTION

The present invention is directed to an isomerized alpha olefin sulfonate. The present invention is also directed to a method of making the isomerized alpha olefin sulfonate.

In one embodiment, the present invention is directed to an isomerized alpha olefin sulfonate having the general formula:

$$R—SO_3M$$

wherein R is an aliphatic hydrocarbyl group having from about 12 to about 40 carbon atoms, having from about 20 to 98 weight percent branching, and containing one or more olefin or alcohol moieties or mixtures thereof; and R is derived from a partially isomerized alpha olefin containing a residual alpha olefin content, wherein when the percent branching in the partially isomerized alpha olefin is less than or equal to 25 weight percent, then the residual alpha olefin content in such partially isomerized alpha olefin is greater than or equal to 8 weight percent; and M is a mono-valent cation.

In one embodiment, the present invention is directed to a method of making an isomerized alpha olefin sulfonate comprising the steps of (a) sulfonating an isomerized alpha olefin with sulfur trioxide in the presence of air thereby producing primarily an isomerized alpha olefin sulfonic acid, wherein the isomerized alpha olefin is derived from the isomerization of $C_{12}$-$C_{40}$ normal alpha olefins;

(b) optionally thermally digesting the product from step (a);

(c) neutralizing the product from step (b) with a source of alkali or alkaline earth metal or amines such as ammonia; and (d) optionally, hydrolyzing the product from step (c) with additional base or caustic.

In one embodiment, the present invention is directed to an isomerized alpha olefin sulfonate having the general formula:

$$R—SO_3M$$

wherein R is an aliphatic hydrocarbyl group having from about 12 to about 40 carbon atoms, having from about 20 to 98 weight percent branching, and containing one or more olefin or alcohol moieties or mixtures thereof; R is derived from a partially isomerized alpha olefin containing a residual alpha olefin content, wherein if the percent branching in the partially isomerized alpha olefin is greater than or equal to 15 weight percent, then the residual alpha olefin content in such partially isomerized alpha olefin is less than or equal to 15 weight percent and wherein if the percent branching in the partially isomerized alpha olefin is less than or equal to 15 weight percent, then the residual alpha olefin content in such partially isomerized alpha olefin is greater than or equal to 15 weight percent; and M is a mono-covalent cation.

DETAILED DESCRIPTION OF THE INVENTION

Definitions

As used herein, the following terms have the following meanings unless expressly stated to the contrary:

The terms "active" or "actives" as used herein refers to the concentration of the metal salt of the sulfonate as described herein.

The term "isomerized alpha olefin (IAO)" as used herein refers to an alpha olefin that has been subjected to isomerization conditions which results in an alteration of the distribution of the olefin species present and/or the introduction of branching along the alkyl chain. The isomerized olefin product may be obtained by isomerizing a linear alpha olefin containing from about 12 to about 40 carbon atoms, and more preferably from about 20 to about 28 carbon atoms.

The term "branching" as used herein refers to alkyl groups along a hydrocarbon chain as measured by infrared spectroscopy.

The term "alkali metal" as used herein refers to Group IA metals of the Periodic Table.

Unless otherwise specified, all percentages are in weight percent and the pressure is atmospheric pressure.

The present invention is directed to an isomerized alpha olefin sulfonate.

The Isomerized Alpha Olefin Sulfonate

The isomerized alpha olefin sulfonate of the present invention has the general formula:

$$R—SO_3M$$

wherein R is an aliphatic hydrocarbyl group having from about 12 to about 40 carbon atoms, having from about 20 to 98 weight percent branching, and containing one or more olefin or alcohol moieties or mixtures thereof; and R is derived from a partially isomerized alpha olefin containing a residual alpha olefin content, wherein when the percent branching in the partially isomerized alpha olefin is less than or equal to 25 weight percent, then the residual alpha olefin content in such partially isomerized alpha olefin is greater than or equal to 8 weight percent; and wherein M is a mono-valent cation. Preferably, M is an alkali metal or ammonium or substituted ammonium ion. Preferably, the alkali metal is sodium.

Examples of substituted ammonium include ammonium independently substituted with from about 1 to about 4 aliphatic or aromatic hydrocarbyl groups having from about 1 to about 15 carbon atoms, such as alkyl, aryl, alkaryl and aralkyl, and optionally having one or more heteroatoms, such as nitrogen, oxygen or sulfur, which may be present in aliphatic or aromatic heterocyclic rings. Examples of suitable heterocyclic ring substituents include pyrrole, pyrrolidine, pyridine, pyrimidine, pyrazole, imidazole and quinoline. The heterocyclic ring substituent may be substituted on the ammonium moiety through a carbon atom in the heterocyclic ring, such as in a C-pyridyl-substituted ammonium, or, alternatively, the quaternary ammonium nitrogen itself may be a nitrogen atom in the heterocyclic ring, such as in a pyridinium ion.

The present invention is directed to a sodium isomerized olefin sulfonate (IOS) made by the sulfonation of an isomerized alpha olefin (IAO) in which the IAO is made by the isomerization of $C_{12}$-$C_{40}$ normal alpha olefins (NAO), preferably $C_{20}$-$C_{28}$ normal alpha olefins, most preferred $C_{20}$-$C_{24}$ normal alpha olefins.

The IAO is composed of between from about 20 to about 98 wt % branching, preferably from about 45 to about 80 wt % branching and most preferred from about 60 to about 70 wt % branching and between from about 0.1 to about 30 wt % residual alpha olefin, preferably between from about 0.2 to about 20 wt % residual alpha olefin and most preferably between from about 0.5 to about 10 wt % residual alpha olefin species.

In one embodiment, the IAO is composed of at least about 23% branching, at least about 9% residual alpha olefin, and having from about 20 to about 24 carbon atoms.

In another embodiment, the IAO is composed of at least about 65% branching, at least about 0.5% residual alpha olefin and having from about 20 to about 24 carbon atoms. Sulfonation of the IAO may be followed by thermal digestion and then neutralization and, optionally hydrolysis, with caustic, in which the resulting sodium isomerized olefin sulfonate (IOS) is composed of between from about 1 to about 50 wt % alcohol sodium sulfonate, preferably from about 3 to about 40 wt % alcohol sulfonate and most preferably from about 5 to about 20 wt % alcohol sulfonate species with the remainder of the sodium sulfonate species being the sodium olefin sulfonate species.

In one embodiment of the present invention, the normal alpha olefins are isomerized using at least one of a solid or liquid catalyst. The NAO isomerization process can be either a batch, semi-batch, continuous fixed bed or combination of these processes using homogenous or heterogenous catalysts. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-1, SSZ-32, ZSM-23, MAPO-39, SAPO-39, ZSM-22 or SSZ-20. Other possible solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl ($Fe(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at about 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of branching.

Sulfonation

Sulfonation of the IAO may be performed by any method known to one of ordinary skill in the art to produce an IAO sulfonic acid intermediate. The sulfonation reaction is typically carried out in a continuous falling film tubular reactor maintained at about 30° C. to about 75° C. The charge mole ratio of sulfur trioxide to olefin is maintained at about 0.3 to 1.1:1.

Other sulfonation reagents, such as sulfuric acid, chlorosulfonic acid or sulfamic acid may also be employed. Preferably, the isomerized alpha olefin is sulfonated with sulfur trioxide diluted with air.

Optionally, the product from the sulfonation process may then be thermally digested by heating.

Neutralization of the Isomerized Alpha Olefin Sulfonic Acid

Neutralization of the IAO sulfonic acid may be carried out in a continuous or batch process by any method known to a person skilled in the art to produce the IOS. Typically, an IAO sulfonic acid is neutralized with a source of a mono-covalent cation. Preferably, the mono-covalet cation is an alkali metal or ammonium or substituted ammonium ion. Preferably, the alkali metal is sodium.

Optionally, the neutralized isomerized alpha olefin sulfonate may be further hydrolyzed with additional base or caustic.

Method of Making an Isomerized Alpha Olefin Sulfonate

A method of making an isomerized alpha olefin sulfonate comprises the steps of (a) sulfonating an isomerized alpha olefin with sulfur trioxide in the presence of air thereby producing primarily an isomerized alpha olefin sulfonic acid, wherein the isomerized alpha olefin is derived from the isomerization of $C_{12}$-$C_{40}$ normal alpha olefins; (b) optionally thermally digesting the product from step (a); (c) neutralizing the product from step (b) with a source of an alkali metal or ammonium; and (d) optionally, hydrolyzing the product from step (c) with additional base or caustic.

The isomerized alpha olefin has from about 12 to about 40 carbon atoms, and from about 20 to 98 weight percent branching; and comprises a partially isomerized alpha olefin containing a residual alpha olefin content, wherein when the percent branching in the partially isomerized alpha olefin is less than or equal to 25 weight percent, then the residual alpha olefin content in such partially isomerized alpha olefin is greater than or equal to 8 weight percent.

The partially isomerized alpha olefin is composed of at least about 23 wt % branching, at least about 9% residual alpha olefin, and having from about 20 to about 24 carbon atoms.

The partially isomerized alpha olefin is composed of at least about 65% branching, at least about 0.2% residual alpha olefin and having from about 20 to about 24 carbon atoms.

In one embodiment, when the partially isomerized alpha olefin is less than or equal to 18 weight percent, then the residual alpha olefin content in such partially isomerized alpha olefin is greater than or equal to 10 weight percent.

Other embodiments will be obvious to those skilled in the art.

The following examples are presented to illustrate specific embodiments of this invention and are not to be construed in any way as limiting the scope of the invention.

EXAMPLE 1

Measurement of % Branching and % Alpha-Olefin in C20-24 Isomerized Alpha Olefins (IAO)

Infrared spectrometry was used to determine the percentage methyl branching and percentage residual alpha-olefin of isomerized C20-24 NAO or isomerized alpha olefin (IAO). The technique involved developing a calibration curve between the infrared absorption at 1378 cm-1 (characteristic of the methyl stretch) measured by attenuated reflectance (ATR) infrared spectrometry and the percent branching determined by Generalized Last Principal Component (GLPC) analysis of the corresponding hydrogenated IAO samples (hydrogenation converts the IAO to a mixture of paraffin's in which the normal paraffin has the longest retention time for a give carbon number). Similarly, a calibration curve was developed between the infrared absorption at 907 cm-1 (characteristic of alpha olefin C—H stretch) determined by attenuated reflectance (ATR) infrared spectrometry and the percent alpha-olefin determined by quantitative carbon NMR.

A linear least squares fit of data for the percent branching showed the following equation:

% Branching by Hydrogenation GC=3.0658 (Peak Height at 1378 cm-1, in mm, by ATR Infrared Spectroscopy)−54.679.

The R2 was 0.9321 and the branching content of the samples used to generate this calibration equation ranged from approximately 9% to 92%.

Similarly, a linear least squares fit of the percent alpha-olefin data showed the following equation:

% Alpha-Olefin by Carbon NMR=0.5082 (Peak Height at 909 cm-1, in mm, by ATR Infrared Spectroscopy)−2.371.

The R2 was 0.9884 and the alpha-olefin content of the samples used to generate this calibration equation ranged from approximately 1% to 75%.

EXAMPLE 2

C20-24 Isomerized Alpha Olefin (IAO)

% Branching versus % Alpha Olefin

The primary olefinic species in Normal Alpha Olefins (NAO's) was normally alpha-olefin. The isomerization of NAO's over the solid acid extrudate catalyst ICR 502 (purchased from Chevron Lummnus Global) isomerized the alpha-olefin to other olefinic species, such as beta-olefins, internal olefins and even tri-substituted olefins. The isomerization of NAO's over ICR 502 catalyst also induced skeletal isomerization in which methyl groups were introduced along the hydrocarbon chain of the isomerized alpha olefin (IAO) which is referred to as branching. Both of the alpha-olefin and branching content of IAO's were conveniently monitored by Infrared spectrometry (Example 1). The degree of olefin and skeletal isomerization of an NAO depends on the conditions of the isomerization process. Table 1 below shows the % residual alpha-olefin vs. the % branching from the isomerization of the C20-24 NAO obtained from Chevron Phillips Chemical Company in a tubular fixed bed reactor (2.54 cm ID×54 cm Length Stainless Steel) packed sequentially from the bottom of the reactor to the top of the reactor as follows: 145 grams Alundum 24, 40 grams of ICR 505 mixed with 85 grams of Alundum 100, 134 grams of Alundum 24. The reactor was mounted vertically in a temperature controlled electric furnace and the NAO was pumped upflow at a weight hourly space velocity (WHSV) of 1.5 while the catalyst bed was held at temperatures ranging between 130° C. and 230° C. at atmospheric pressure and samples of IAO were collected at the outlet of the reactor.

TABLE 1

| Wt. % Branching | Wt. % Residual Alpha-Olefin |
|---|---|
| 4.4 | 68.8 |
| 7.7 | 40 |
| 8.1 | 47.5 |
| 8.1 | 43.2 |
| 8.3 | 55.3 |
| 8.9 | 45.3 |
| 9.1 | 40.4 |
| 10.9 | 41.2 |
| 12.7 | 34.4 |
| 12.8 | 26.2 |
| 12.8 | 26.9 |
| 14 | 22.3 |
| 14.6 | 19.4 |
| 14.8 | 15.5 |
| 14.8 | 17.7 |
| 15 | 19.2 |
| 16 | 17 |
| 16.4 | 15.1 |
| 16.6 | 13.8 |
| 16.9 | 14.8 |
| 17.3 | 12.3 |
| 17.5 | 13.6 |
| 17.6 | 15.3 |
| 18.7 | 6.7 |
| 18.9 | 8.7 |
| 18.9 | 16.5 |
| 19.1 | 7 |
| 19.1 | 8.2 |
| 19.7 | 9 |
| 19.8 | 10.8 |
| 20 | 16.5 |
| 20 | 16.3 |
| 20.3 | 7.7 |
| 20.3 | 13.3 |
| 20.5 | 10.2 |
| 20.5 | 14.5 |
| 20.5 | 13.1 |
| 20.6 | 17.1 |
| 20.7 | 12.6 |
| 20.7 | 14 |
| 20.7 | 14.2 |
| 20.8 | 16.8 |
| 20.9 | 12.5 |
| 20.9 | 14.1 |
| 21.2 | 8.7 |

TABLE 1-continued

| Wt. % Branching | Wt. % Residual Alpha-Olefin |
|---|---|
| 21.3 | 13.6 |
| 21.8 | 14.4 |
| 22.2 | 11.1 |
| 22.2 | 12.6 |
| 22.2 | 12.9 |
| 22.4 | 11.4 |
| 22.4 | 4 |
| 22.6 | 3.7 |
| 22.6 | 10.7 |
| 22.6 | 11.6 |
| 23.6 | 9.8 |
| 23.6 | 9.5 |
| 23.8 | 2.8 |
| 24.6 | 1.8 |
| 24.8 | 1.9 |
| 25 | 9.4 |
| 26.6 | 4.9 |
| 27.9 | 3.2 |
| 28.2 | 0.7 |
| 28.2 | 0.7 |
| 29 | 2.5 |
| 29.4 | 2 |
| 29.7 | 2.7 |
| 29.8 | 2.3 |
| 30.3 | 1 |
| 33.4 | 1 |
| 33.6 | 0.8 |
| 34.3 | 1.1 |
| 34.5 | 2.5 |
| 36.9 | 1.1 |
| 40.6 | 1 |
| 41.8 | 0.8 |
| 42.8 | 0.8 |
| 43 | 0.8 |
| 43.2 | 1 |
| 44 | 1 |
| 44 | 1 |
| 48.8 | 1 |
| 50.8 | 0.4 |
| 51.8 | 0.6 |
| 52.3 | 1 |
| 52.4 | 2.5 |
| 52.8 | 0.5 |
| 54.9 | 1 |
| 55.4 | 1 |
| 55.5 | 1 |
| 55.5 | 0.4 |
| 57.7 | 1 |
| 59.2 | 1 |
| 61 | 0.4 |
| 61.2 | 1 |
| 61.5 | 1 |
| 61.6 | 1 |
| 61.6 | 1 |
| 62.3 | 1 |
| 62.8 | 1 |
| 63.5 | 1 |
| 63.6 | 1 |
| 64.7 | 1 |
| 64.8 | 0.3 |
| 65.7 | 0.3 |
| 66 | 1 |
| 67 | 1 |
| 67.2 | 1 |
| 67.5 | 1 |
| 67.5 | 0.3 |
| 67.7 | 0.4 |

TABLE 1-continued

| Wt. % Branching | Wt. % Residual Alpha-Olefin |
|---|---|
| 67.8 | 1 |
| 68 | 1 |
| 68.5 | 0.3 |
| 68.6 | 1 |
| 68.6 | 1 |
| 68.6 | 1 |
| 69 | 1 |
| 69.3 | 1 |
| 69.4 | 1 |
| 70.2 | 0.4 |
| 70.4 | 1 |
| 70.6 | 0.4 |
| 71.6 | 1 |
| 71.8 | 1 |
| 72 | 1 |
| 72 | 1 |
| 72.2 | 1 |
| 72.4 | 1 |
| 73.8 | 1 |
| 75.8 | 1 |
| 79.6 | 0.4 |
| 81.2 | 0.3 |
| 94.7 | 0.3 |
| 95.9 | 0.3 |
| 97.1 | 0.4 |

For comparison, the isomerized C20-22 obtained from Shell Chemical company shows 10.7% Branching and 8.2% residual Alpha-Olefin content and.

EXAMPLE 3

Sulfonation of Branched C20-24 Isomerized Alpha Olefins (IAO's)

Isomerized C20-24 alpha olefin (IAO) feeds containing varying amounts of branching and alpha-olefin obtained from Example 2, were sulfonated in a glass, water jacketed, falling film tubular reactor (0.6 cm ID and three reactors in series, R1=30 cm, R2=30 cm and R3=70 cm) using SO3/Air and the following conditions:

IAO Feed Temperature=50° C.

Reactor Temperature=30° C.

Air Flow=192 liters/hr

SO2 Flow=16 liters/hr

SO2 to SO3 conversion=87%

The IAO feed rate was varied to obtain the desired charge molar ratio of S03 to IAO. The crude isomerized olefin sulfonic acid was then optionally digested in air at varying temperatures and times with mechanical (magnetic stir bar) agitation in an open beaker. The resulting isomerized olefin sulfonic acid was then analyzed by cyclohexylamine titration. Table 2 illustrates the properties of IAO's and corresponding olefin sulfonic acids obtained.

TABLE 2

| | IAO Properties | | | | | IAO Sulfonic Acid Properties | |
|---|---|---|---|---|---|---|---|
| | | Alpha- | Sulfonation | Digestion Conditions | | | |
| Entry | Branching (%) | Olefin (%) | CMR SO3/IAO | Temperature (° C.) | Time (minutes) | SO3H (%) | H2SO4 (%) |
| 1 | 17.0 | 0.4 | 0.8 | 40 | 20 | 30.4 | 1.1 |
| 2 | 23.0 | 9.2 | 0.8 | 40 | 20 | 49.7 | 0.9 |
| 3 | 23.0 | 9.2 | 0.9 | 40 | 20 | 51.9 | 1.1 |
| 4 | 23.0 | 9.2 | 1.0 | 40 | 20 | 49.7 | 1.6 |
| 5 | 48.3 | 0.5 | 0.8 | 40 | 20 | 54.2 | 1.2 |
| 6 | 48.3 | 0.5 | 0.9 | 40 | 20 | 56.5 | 1.4 |
| 7 | 48.3 | 0.5 | 1.0 | 40 | 20 | 56.5 | 1.9 |
| 8 | 65.0 | 0.5 | 0.8 | 40 | 20 | 61.0 | 1.4 |
| 9 | 65.0 | 0.5 | 0.9 | 40 | 20 | 64.5 | 1.9 |
| 10 | 65.0 | 0.5 | 1.0 | 40 | 20 | 67.7 | 2.6 |
| 11 | 65.1 | 0.4 | 0.8 | 40 | 0 | 58.9 | 0.8 |
| 12 | 65.1 | 0.4 | 0.8 | 40 | 20 | 58.9 | 1.1 |
| 13 | 65.1 | 0.4 | 0.8 | 40 | 40 | 58.6 | 1.2 |
| 14 | 65.1 | 0.4 | 0.8 | 40 | 60 | 58.4 | 1.2 |
| 15 | 65.0 | 0.4 | 0.8 | 40 | 30 | 62.6 | 1.1 |
| 16 | 65.0 | 0.4 | 0.8 | 80 | 30 | 47.2 | 2.5 |
| 17 | 65.0 | 0.4 | 0.8 | 120 | 30 | 14.5 | 0.4 |
| 18 | 94.4 | 0.3 | 0.8 | 40 | 20 | 44.0 | 1.0 |
| 19 | 94.4 | 0.3 | 0.9 | 40 | 20 | 49.0 | 1.3 |
| 20 | 94.4 | 0.3 | 1.0 | 40 | 20 | 52.2 | 1.5 |

EXAMPLE 4

Neutralization of C20-24 Isomerized Alpha Olefin (IAO) Sulfonic Acids

Isomerized alpha olefin (IAO) sulfonic acids obtained from Example 3 were neutralized by the successive addition of aliquouts (typically between 1 and 3 grams each) of 50 wt % aqueous NaOH to the IAO sulfonic acid over approximately 45 minutes to 80 minutes at between 25 and 40° C. with mechanical stirring (approximately 340 rpm). The resulting sodium alpha olefin sulfonates (IOS's) were analyzed and found to have the following properties as shown in Table 3:

TABLE 3

| Entry | IAO Sulfonic Acid from Example 3 | Product pH | Wt. Average MW (1) (Daltons) | Activity (2) (%) | Hydroxy Sulfonate Content (3) (%) |
|---|---|---|---|---|---|
| A | Entry 1 | 10.5 | 385 | — | 27.7 |
| B | Entry 2 | 10.9 | 410 | 30.3 | 28.1 |
| C | Entry 3 | 7.8 | 413 | 34.5 | 37.9 |
| D | Entry 4 | 10.1 | 408 | 37.3 | 27.9 |
| E | Entry 5 | 11.2 | 410 | 42.3 | 15.7 |
| F | Entry 6 | 10.4 | 406 | 43.9 | 11.1 |
| G | Entry 7 | 11.2 | 405 | 44.3. | 10.9 |
| H | Entry 8 | 10.2 | 402 | 47.2 | 2.6 |
| I | Entry 9 | 10.7 | 402 | 49.4 | 3.7 |
| J | Entry 10 | 10.6 | 401 | 50.4 | 4.1 |
| K | Entry 18 | 10.8 | 405 | 35.2 | 5.2 |
| L | Entry 19 | 10.6 | 408 | 38.9 | 5.6 |
| M | Entry 20 | 10.4 | 406 | 40.7 | 5.7 |

(1) Weight Average Molecular Weight was determined from Electro-Spray Ionization Mass Spectrometry (ESI-MS)

(2) Activity was determined by Hyamine Titration using the weight average molecular weight determined by ESI-MS (3) The % Hydroxy Sulfonate was determined by Electro-Spray Ionization Mass Spectrometry (ESI-MS).

EXAMPLE 5

Sulfonation of 65% Branched C20-24 Isomerized Alpha-Olefin

Isomerized C20-24 alpha-olefin containing 65% branching and 0.5% alpha-olefin obtained from the isomerization of C20-24 normal alpha-olefin (purchased from Chevron Philips Company) in a fixed bed reactor containing the solid acid extrudate catalyst ICR 502 (purchased from Chevron Lummnus Global) at atmospheric pressure in up-flow mode at a WHSV of approximately 0.7. The C20-24 was pre-heated by means of a heat exchanger and the catalyst bed temperature ranged between 187° C. and 190° C. was sulfonated in a vertical, falling film reactor (water jacketed stainless steel, 0.6 inch ID, 5 feet long) using concurrent SO3/Air down flow, a cyclone separator where a portion of the acid is cooled acid and recycled to the bottom of the falling film reactor. The crude acid is optionally digested by passing through a water jacked, plug flow vessel at 40° C. and neutralized by the addition of 50 wt. % aqueous NaOH by means of tee inlet followed by passing the neutralized acid through a high sheer mixer at 85-90° C. The following sulfonation and digestion conditions were used (See Table 4):

| | |
|---|---|
| Air/$SO_3$ Temperature, ° C. | 38 |
| IAO Feed Temperature, ° C. | 25 |
| Reactor Temperature, ° C. | 30 |
| $SO_3$ in Air Concentration, Vol % | 2.5 |
| $SO_3$ Reactor Loading, kg/hr-cm | 0.777 |

TABLE 4

| | MR | Digestion | FLOWRATES | |
|---|---|---|---|---|
| Condition Number | $SO_3$/ IAO | Time (minutes) | $SO_3$ kg/hr | IAO Feed kg/hr |
| 1 | 1.0 | none | 3.72 | 13.978 |
| 2 | 0.8 | none | 3.72 | 17.473 |

TABLE 4-continued

| Condition Number | MR SO$_3$/ IAO | Digestion Time (minutes) | FLOWRATES SO$_3$ kg/hr | IAO Feed kg/hr |
|---|---|---|---|---|
| 3 | 0.7 | none | 3.72 | 19.969 |
| 4 | 0.6 | none | 3.72 | 23.297 |
| 5 | 0.9 | none | 3.72 | 15.532 |
| 6 | 0.9 | 30 | 3.72 | 15.532 |

The following properties of the intermediate isomerized alpha olefin sulfonic acid (IAO Sulfonic Acid) and the corresponding sodium salt (IOS Sodium Salt) following neutralization were obtained (See Table 5):

TABLE 5

| | IAO Sulfonic Acid Properties | | | Sodium IOS Properties | | | |
|---|---|---|---|---|---|---|---|
| Condition Number | RSO$_3$H (%) | $H_2SO_4$ (%) | Acid Number (mg KOH/ gm of Sample) | Hyamine Activity (%) (1) | Hydroxy Sulfonate, (%) (2) | pH (3) | Free Base (%) |
| 1 | 60.9 | 2.1 | 113.5 | 70.4 | 25.7 | 9.7 | 0.77 |
| 2 | 59.8 | 1.1 | 101.1 | 71.8 | 23.0 | 9.8 | 0.69 |
| 3 | 55.4 | 0.6 | 88.7 | 66.2 | 12.0 | 9.7 | 0.69 |
| 4 | 55.9 | 0.4 | 88.9 | 68.3 | 8.7 | 9.5 | 0.80 |
| 5 | 61.4 | 1.5 | 107.4 | 73.9 | 20.5 | 9.5 | 0.69 |
| 6 | 60.9 | 1.6 | 108.4 | 66.5 | 12.9 | 9.7 | 0.69 |

(1) Calculated using a weight average molecular weight of 403.
(2) Determined by electro-spray ionization mass spectrometry (ESI-MS).
(3) Determined on approximately a 1 wt. % sodium IOS in water using a calibrated (pH 7 and 10) pH electrode.

The IOS sodium salts obtained following neutralization were then subjected to hydrolysis conditions. The general hydrolysis procedure involves weighing 30 grams of the IOS sodium salt into a 50 ml mechanically stirred pressure reactor (Parr Model 4590 Micro Bench Top Reactor equipped with a Parr Model 4843 temperature controller), adding a specified amount of 50 wt. % aqueous NaOH, initiating stirring (approximately 200 rpm) and increasing the temperature to the desired hydrolysis temperature (typically over 15-25 minutes), holding the reactor contents at the desired temperature followed by cooling to room temperature and removing the contents of the reactor. Using this procedure to hydrolyze the sodium IOS's obtained above afforded products with the following properties (See Table 6):

TABLE 6

| Condition Number | Hydrolysis Temperature (° C.) | Hydrolysis Time (hours) | Amount of Base added per 30 grams of IOS Sodium Salt | Hydrolyzed Sodium IOS Hyamine Activity (%) (1) | Hydroxy Sulfonate, (%) (2) |
|---|---|---|---|---|---|
| | Hydrolyzed Sodium IOS Properties | | | | |
| 1 | 120 | 0.5 | 2..0 | 75.8 | 27.4 |
| 2 | 120 | 0.5 | 2.0 | 73.1 | 19.8 |
| 3 | 120 | 0.5 | 2.0 | 67.3 | 13.8 |
| 4 | 120 | 0.5 | 2.0 | 60.1 | 11.7 |
| 5 | 120 | 0.5 | 2.0 | 72.4 | 22.6 |
| 5 | 140 | 0.5 | 2.0 | 67.3 | 27.6 |
| 5 | 160 | 0.5 | 2.0 | 67.7 | 22.7 |
| 5 | 120 | 0.5 | 1.0 | 70.1 | 24.6 |
| 5 | 120 | 0.5 | 1.5 | 73.4 | 23.5 |
| 5 | 120 | 1.0 | 2.0 | 72.3 | 23.7 |
| 6 | 120 | 0.5 | 2.0 | 73.8 | 15.4 |

EXAMPLE 6

Isomerized C20-28 Alpha Olefin (IAO)

Fixed Bed Process

A mixture of C20-24/C26-28 NAO (70:30 blend by weight respectively obtained from Philllips Chemical Company) was isomerized by passing the NAO blend through a fixed bed reactor as described in Example 2 at a WHSV of 1.2. Product was collected with time and samples analyzed to approximate (since the data used in Example 1 is for C20-24 IAO) the percent branching using the method of Example 1. The temperature of the catalyst bed was gradually increased over 36 hours from 221° C. to 223° C. to maintain the branching at approximately 65%. The final product obtained contained 66.5% branching and 0.5% residual alpha-olefin.

EXAMPLE 7

Isomerized C20-28 Alpha Olefin (IAO)

Batch Process

Four liters (approximately 3.2 kg) of a mixture of C20-24/C26-28 NAO (80:20 blend by weight respectively obtained from Phillips Chemical Company) was added to a 10 liter, glass, round bottom flask fitted with a mechanical stirrer, reflux condenser and a thermocouple under a dry nitrogen atmosphere. To this mixture was added 25 grams of dry ICR 502 catalyst, as used in Example 2. The reaction temperature was gradually raised from 150° C. to 180° C. using a temperature controller over approximately 10 days. Aliquots from the reaction flask were analyzed with time to determine the approximate (since the data used in Example 1 is for C20-24 IAO) percent branching and alpha olefin by infrared spectroscopy using the method of Example 1. Additional ICR 502 catalyst was added after approximately 7 days (40 grams). The final product contained approximately 85.1% branching and 0.2% residual alpha-olefin by the method of Example 1.

EXAMPLE 8

Sulfonation of C20-28 IAO Containing 85.1% Branching and 0.2% Alpha-Olefin

Isomerized C20-28 alpha-olefin (IAO) containing 85.1% branching and 0.2% alpha-olefin obtained from Example 7 was sulfonated as in Example 3 using the following conditions:

IAO Feed Temperature=30° C.
Reactor Temperature=30° C.
Air Flow=192 liters/hr
SO2 Flow=16 liters/hr
SO2 to SO3 conversion=87%

The resulting isomerized alpha-olefin (IAO) sulfonic acids obtained were then digested at 40° C. for 20 minutes with mechanical (magnetic stir bar) agitation in an open beaker and then analyzed by cyclohexylamine titration. The IAO sulfonic acids obtained were then neutralized by the successive addition of aliquouts (typically between 1 and 3 grams each) of 50 wt % aqueous NaOH to the IAO sulfonic acid over approximately 45 minutes to 80 minutes at between 35 and 40° C. with mechanical stirring (approximately 340 rpm). The resulting sodium alpha olefin sulfonates (IOS's) were analyzed and found to have the following properties (See Table 7):

TABLE 7

| | IAO | Digested IAO | | Neutralized IOS Properties | | | |
|---|---|---|---|---|---|---|---|
| | Sulfonation Conditions | Sulfonic Acid Properties | | | Wt. Average | Activity | Hydroxy Sulfonate |
| Entry | CMR SO3/IAO | SO3H (%) | H2SO4 (%) | pH (4) | MW (1) (Daltons) | (2) (%) | Content (3) (%) |
| 1 | 0.8 | 41.4 | 4.1 | 10.1 | 417 | 33.5 | 2.5 |
| 2 | 0.9 | 40.8 | 5.3 | 10.1 | 415 | 32.0 | 2.2 |
| 3 | 1.0 | 35.7 | 6.5 | 9.3 | 416 | 28.0 | 2.3 |

(1) Weight Average Molecular Weight was determined from Electro-Spray Ionization Mass Spectrometry (ESI-MS)

(2) Activity was determined by Hyamine Titration using the weight average molecular weight determined by EDI-MS (3) The % Hydroxy Sulfonate was determined by Electro-Spray Ionization Mass Spectrometry (ESI-MS).

(4) Determined on approximately a 1 wt. % sodium IOS in water using a calibrated (pH 7 and 10) pH electrode

What is claimed is:

1. An isomerized alpha olefin sulfonate of the formula:

$$R—SO_3M$$

wherein R is an aliphatic hydrocarbyl group having from about 12 to about 40 carbon atoms, having from about 20 to 98 weight percent branching, and containing one or more olefin or alcohol moieties or mixtures thereof; and R is derived from a partially isomerized alpha olefin containing a residual alpha olefin content, wherein when the percent branching in the partially isomerized alpha olefin is less than or equal to 25 weight percent, then the residual alpha olefin content in such partially isomerized alpha olefin is greater than or equal to 8 weight percent; and M is a mono-valent cation.

2. The isomerized alpha olefin sulfonate of claim 1 wherein the partially isomerized alpha olefin is composed of at least about 23 wt % branching, at least about 9% residual alpha olefin, and having from about 20 to about 24 carbon atoms.

3. The isomerized alpha olefin sulfonate of claim 1 wherein the partially isomerized alpha olefin is composed of at least about 65% branching, at least about 0.2% residual alpha olefin and having from about 20 to about 24 carbon atoms.

4. The isomerized alpha olefin sulfonate of claim 1 wherein when the percent branching in the partially isomerized alpha olefin is less than or equal to 18 weight percent, then the residual alpha olefin content in such partially isomerized alpha olefin is greater than or equal to 10 weight percent.

5. An isomerized alpha olefin sulfonate of the formula:

$$R—SO_3M$$

wherein R is an aliphatic hydrocarbyl group having from about 12 to about 40 carbon atoms, having from about 20 to 98 weight percent branching, and containing one or more olefin or alcohol moieties or mixtures thereof; and R is derived from a partially isomerized alpha olefin containing a residual alpha olefin content, wherein if the percent branching in the partially isomerized alpha olefin is greater than or equal to 15 weight percent, then the residual alpha olefin content in such partially isomerized alpha olefin is less than or equal to 15 weight percent and wherein if the percent branching in the partially isomerized alpha olefin is less than or equal to 15 weight percent, then the residual alpha olefin content in such partially isomerized alpha olefin is greater than or equal to 15 weight percent; and M is a mono-valent cation.

* * * * *